United States Patent [19]
Klein

[11] 4,038,753
[45] Aug. 2, 1977

[54] ORTHODONTIC APPARATUS INCLUDING UNITARY DISPENSER AND DISPENSED ARTICLES

[75] Inventor: Paul E. Klein, Lake Oswego, Oreg.

[73] Assignee: Modcom, Inc., Clackamas, Oreg.

[21] Appl. No.: 611,017

[22] Filed: Sept. 8, 1975

Related U.S. Application Data

[63] Continuation of Ser. No. 468,529, May 9, 1974, abandoned.

[51] Int. Cl.² ............................................. A61C 7/00
[52] U.S. Cl. .......................................... 32/14 E; 32/66
[58] Field of Search .............. 206/339, 820, 343, 345, 206/815; 224/28 F; 32/14

[56] References Cited

U.S. PATENT DOCUMENTS

| | | | |
|---|---|---|---|
| 1,286,610 | 12/1918 | Harriman | 224/28 F |
| 2,737,181 | 3/1956 | Beard | 128/303 A |
| 3,193,094 | 7/1965 | Schultstad | 206/63.5 |
| 3,530,583 | 9/1970 | Klein et al. | 32/14 A |

*Primary Examiner*—Robert Peshock
*Attorney, Agent, or Firm*—Kolisch, Hartwell, Dickinson & Stuart

[57] ABSTRACT

A molded unitary elastomeric orthodontic product which takes the form of a digitally manipulatable dispensing tool, placeable adjacent and within a person's mouth, and joined integrally yet severably with this tool a plurality of dispensable orthodontic intraoral tension-applying devices.

11 Claims, 8 Drawing Figures

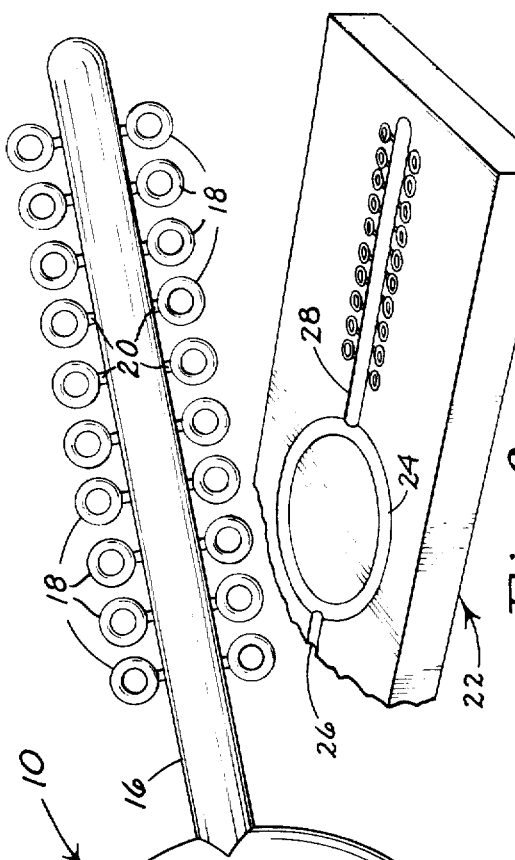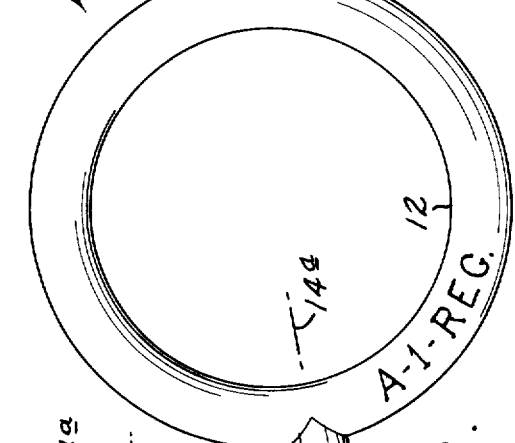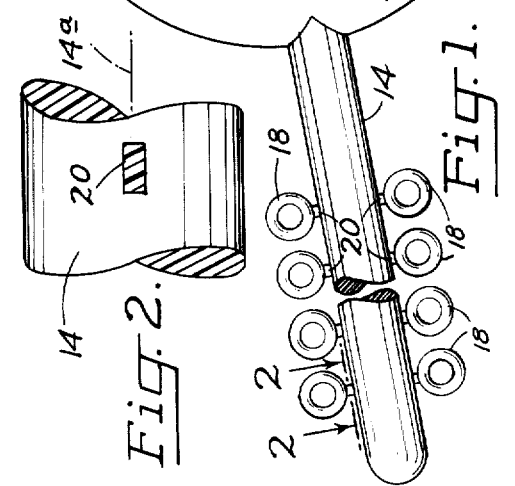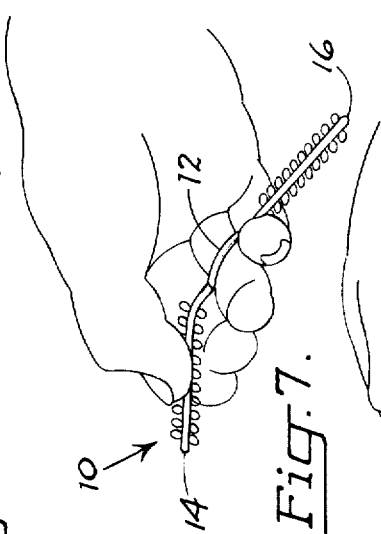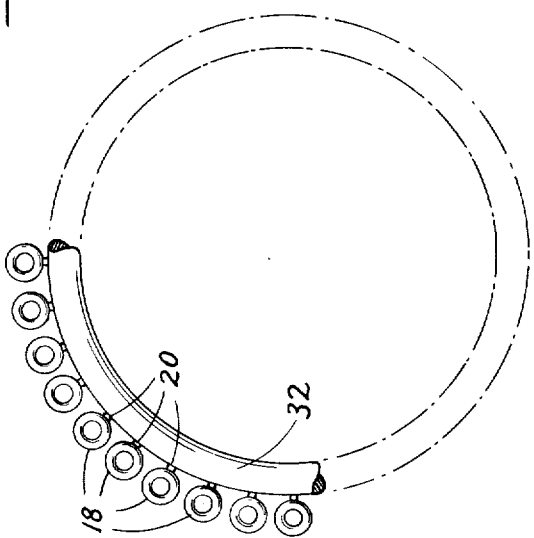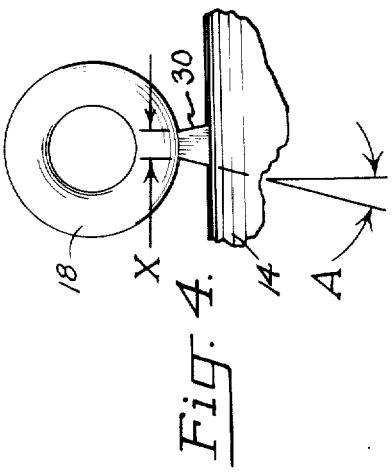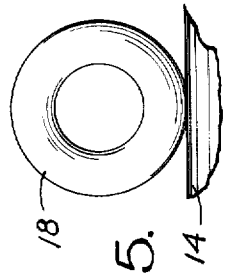

ORTHODONTIC APPARATUS INCLUDING UNITARY DISPENSER AND DISPENSED ARTICLES

CROSS REFERENCE TO PRIOR APPLICATION

This invention is a continuation of my prior-filed application entitled "Orthodontic Apparatus Including Unitary Dispenser and Dispensed Articles", filed May 9, 1974, Ser. No. 468,529, now abandoned.

BACKGROUND AND SUMMARY OF THE INVENTION

This invention pertains to an orthodontic product, and more particularly to such a product which includes a plurality of dispensable intraoral tension-applying devices formed integrally, yet severably with a digitally manipulatable dispensing tool, which is sized and shaped to be used conveniently adjacent and within a patient's mouth. The tension-applying devices contemplated are of the type which are configured to be hooked onto an external structure, such as a bracket, within a person's mouth.

Recent years have seen the ever-increasing use, by orthodontists, or a relatively wide variety of small, differently sized and shaped, molded elastomeric intraoral tension-applying devices. These devices are used, for example, to apply intra- and inter-maxillary forces for correcting both the relative positions of a person's teeth within a given jaw, as well as the relative positions of the upper and lower jaws. A typical device of the type under consideration includes one or more generally circular rings which, when used in a person's mouth, are stretched over hooks, or brackets, attached to teeth bands, or the like, disposed in the mouth.

Conventional practice with respect to the manufacture and packaging of such devices is to produce a given type device as a separate unit, which is then packaged along with a certain number of other like units for sale to the user—e.g., the orthodontist. An individual device so produced is far too small, as a practical matter, for it to be marked individually to indicate its specific size and type designation. The packages, however, are marked. Thus, it is important, if confusion is to be avoided, that such packages be handled carefully so that the devices do not become accidentally separated, and hence difficult to identify or return to their proper package. Devices which do become accidentally separated, as by spillage, are difficult to identify inasmuch as they may differ only slightly in appearance from neighboring size devices. Hence, there are clearly some practical disadvantages to the conventional way, just described, of producing and marketing devices of the type being discussed.

Still another drawback concerns the amount of manipulation, and time consumption, used with respect to preparing a device for use within a person's mouth. Typically, the orthodontist, or someone under his direction, selects the particular appropriate device which is to be used, removes it carefully from its package, and then mounts it on the tool which is to be used to position it in the mouth. Those who are familiar with this practice are aware that, in view of the relatively small sizes which characterize these devices, the procedure just described can be quite time-consuming, and sometimes frustrating.

A general object of the present invention is to provide a novel orthodontic product of the type generally outlined (in the first paragraph under this heading), which product takes care of the several drawbacks just mentioned in a highly practical and satisfactory manner.

More particularly, an object of the invention is to provide such a product which minimizes the identification and loss problems discussed, and which further avoids the necessity for transferring a device onto a tool before use in a person's mouth.

According to a preferred embodiment of the invention, what is contemplated is a molded unitary product, formed of a suitable elastomeric material, and including a digitally manipulatable carrier, which acts as a dispensing tool in the product, to which are integrally and severably joined, through break-away molded joints, a plurality of tension-applying devices usable (with other orthodontic apparatus) in a person's mouth.

As will be explained below, the overall configuration of the final product may have different shapes to suit different needs. One shape may include, as a part of the carrier in the product, an elongated portion, referred to as a dispensing portion, along which are distributed the specific devices which are to be dispensed. Another shape may take the form of an enless band which acts as the carrier for devices. Ordinarily, a given product will carry only devices of one specific size and type, which size and type are clearly marked on the carrier so that identification is easy. However, it is appreciated that it might, in certain circumstances, be desirable to provide a product having, at different selected locations, different types of devices, also appropriately marked on the carrier.

It will be evident that with a product of the type outlined, packaging, marking, loss and identification essentially disappear as problems since the devices remain with the carrier until use. Further, with the carrier in the product constructed to act as the tool used for placement of devices, transfer of a device to a separate special tool is not required.

The joints mentioned are configured, as will be described, to permit snap-action severing, or separation, of a device from the carrier, without any damage to the severed device.

These and other objects and advantages attained by the invention will become more fully apparent as the description which follows is read in conjunction with the accompanying drawings.

DESCRIPTION OF THE DRAWINGS

FIG. 1 is a side elevation, on a larger than true-life scale, illustrating, fragmentarily, one form of the invention as contemplated herein.

FIG. 2 is an enlarged cross section taken generally along the line 2—2 in FIG. 1.

FIG. 3 is a reduced-scale simplified fragmentary view, in perspective, illustrating a portion of the mold which was used to form the article depicted in FIG. 1.

FIGS. 4 and 5, which are on about the same scale as FIG. 2, illustrate two different modifications of break-away joints or connections which are used according to the invention.

FIG. 6 illustrates a modified form of the invention.

And, FIGS. 7 and 8 illustrate generally how the articles of FIGS. 1 and 6, respectively, would be held typically during use.

DETAILED DESCRIPTION OF THE INVENTION

Turning now to the drawings, and referring first to FIGS. 1 and 2, indicated generally at 10 is a unitary, elastomeric orthodontic article, or apparatus, constructed in accordance with the present invention. The material used herein for forming article 10 is a commercially available thermoset-thermoplastic, polyester-based, isocyanate-terminated, urethane resin.

In the form of the invention shown in FIG. 1, article 10 comprises what is referred to herein as a carrier, or carrier portion, including a central ring 12 to which are integrally joined a pair of radially outwardly projecting, diametrically opposed elongated fingers, prongs, or dispenser portions, 14, 16. The carrier is also referred to herein as a runner. Joined to and distributed along opposite sides of each finger are a plurality of orthodontic intraoral tension-applying devices 18 which, herein, take the form of generally circular rings. In the embodiment shown in FIG. 1, rings 18 are joined to fingers 14, 16 through elongated break-away isthmuses, or gates, 20 which preferably have uniform cross sections along their lengths, with these cross sections being nonsquare rectangular as shown in FIG. 2. In article 10, devices 18 and gates 20 lie generally in the plane of FIG. 1 although this is not a critical or limiting factor. As can be seen in FIG. 2, which shows the cross section of a gate, the long dimension of this cross section substantially parallels the longitudinal axis of finger 14, which axis is shown at 14a. Although the specific dimensions of ring 12 and fingers 14, 16 are not critical, in article 10 ring 12 has a diameter of about 1 inch, and fingers 14, 16 each have a length of about 3 inches. The cross sections of the ring and fingers, which are circular, each have a diameter of about $\frac{1}{8}$ inch.

Ring-like devices 18 are shown herein only for the purpose of illustration—it being understood that a relatively wide variety of orthodontic tension-applying devices could be carried at the locations of devices 18. The devices shown have an inside diameter of about 1/32 inches, and a cross—sectional diameter also of about 1/32 inches.

Preferably, each gate 20 has a length, extending between its associated finger and device, of about 0.005 inches, with its cross-sectional dimensions being about 0.015 inches by about 0.032 inches.

Article 10 herein has been formed by a molding process, although this is not considered to be a limiting factor of the invention. In other words, molding has been found to be an extremely simple and economical way of producing an article such as article 10, but it is recognized that there are perhaps other production techniques which could be used.

Indicated generally at 22 in FIG. 3, fragmentarily, is a portion of one section, or side, of the mold which was used to form article 10. Thus, included in this section of the mold, on the upper surface thereof in FIG. 3, are a central circular trough 24 from which radiate, on diametrically opposite sides thereof, elongated straight troughs 26, 28. Troughs 24, 26, 28 complemented by the corresponding troughs in the other section of the mold which is not shown, cooperated to form ring 12 and fingers 14, 16, respectively, during the molding operation which produced article 10. Suitable means (not shown) is, of course, provided for introducing liquid resin into the mold. Also formed in the mold section shown are suitable recesses communicating with troughs 26, 28 for the formation of devices, like devices 18, and gates, like gate 20.

It will thus be apparent that the paths or troughs in a mold through which resin is introduced to form the devices which are ultimately to be used in a patient's mouth may also be used to form a dispensing carrier or tool on which these devices may remain conveniently until it is time for their use.

It will typically be the case that a given article, such as article 10, will carry but a single type and size of orthodontic device, though this need not always be the case. Regardless of whether this is the case, however, it will be evident that it is a relatively simple matter to include, within the mold, suitable markings which will permanently mark either on ring 12 or on one or both of fingers 14, 16, appropriate designations which will positively identify the types and sizes of carried orthodontic devices. Such an identification is shown herein in FIG. 1, molded into the bottom side of ring 12.

While variations in the general shape of article 10 are possible, as, for example, by including more fingers than the two shown, or by orienting fingers at different angles, the specific form illustrated has been found to be an especially convenient and handy one for use. More specifically, a typical way of handling and using article 10 is shown in FIG. 7 which illustrates ring 12 slipped over the ring finger of the right hand of the user, with finger 14 grasped between the thumb and forefinger, and finger 16 extending freely downwardly from ring 12. When it is desired to position a device 18 in a patient's mouth, the end of a finger is simply inserted in the mouth to position an outer device 18 properly, which is then hooked in place through stretching it over the hook or bracket, or whatever, to which it is to be attached. A quick sharp snap or pull of the finger away from the device then causes the device to sever or break away from the finger at the location of the connecting gate 20.

Experimentation and experience has shown that gates constructed like gates 20 in FIGS. 1 and 2, when subjected to the snapping or pulling action just described, will predictably break at a point therein located slightly toward the associated finger from the associated device. In other words, the snapping action used to sever a device will not result in tearing of a portion of the device which might damage it.

With respect to an article like article 10, as successive devices are removed from a finger, it may be desirable progressively to cut off that remaining portion of the finger which projects beyond any remaining devices, thus to facilitate maneuvering and placement of those devices 18 which are progressively closer to ring 12. Further, if an orthodontist may, with respect to a given patient's mouth, be using several different types of devices in a relatively short span of time, he may simultaneously carry on his finger different articles like article 10 carrying the different required devices. With this procedure it will be obvious that it will be a relatively easy matter for the orthodontist to select very rapidly, and install, the different desired devices.

FIGS. 4 and 5 illustrate modified structure which may be used in place of gates 20 to join a device and a finger. In FIG. 4, a gate 30 is shown joining a device 18 and finger 14. The side of gate 30 which faces the viewer in FIG. 4, and the opposite nonviewable side each lie in a plane which substantially parallels the plane of FIG. 4. The other two sides, however, converge symmetrically progressing from the finger toward the device. The slope angle of these sides, indicated at A, has been found to be best if lying within the range of about 15 to 60°. The dimension, shown at X, at the location where a gate 30 joins the device is preferably about 0.018 inches. Also, the length of the gate, between finger 14 and device 18, is preferably about 0.018 inches.

Snapping or pulling action as described earlier to sever a device, when gates like gate 30 are present, has been found to produce about the same effect as with gates 20.

FIG. 5 illustrates a direct tangential joinder between a device 18 and finger 14. Experience has shown that this type of joinder will also result in snap-action breakaway without damaging the removed device. Preferable, however, to the modifications shown in FIGS. 4 and 5, are gates like gates 20.

FIG. 6 in the drawings illustrates another modified form of an orthodontic article, wherein the carrier or tool portion takes the form of an endless band such as band 32. Orthodontic devices are distributed circumferentially about the outside of the band, as shown.

FIG. 8 illustrates how an article like that shown in FIG. 6 might be used, with band 32 extending around the fingers as shown, and with the thumb and forefinger positioned to maneuver a device to the proper location within a person's mouth.

It will thus be apparent that the present invention offers a number of decided advantages. Orthodontic devices are not packaged as individuals, and thus are not subject to loss or confusion with other similar devices. Their identification may readily be marked on the carrier which carries them, which carrier also functions as a tool for placing the devices in a person's mouth, and for enabling dispensing of these devices. It should be appreciated that the two different types of articles illustrated herein, along with the several modifications suggested for article 10, are not exhaustive of the different shapes which might have utility in different applications. Further, dimensions different than those expressed above may be found to be just as satisfactory. The essence of the invention does not reside in any specific configuration or size, but rather in the concept of having unitarily joined carrying (and dispensing) tools with severably joined dispensable intraoral devices.

Thus, while several embodiments of the invention have been shown and described herein, and certain modifications suggested, it is appreciated that a number of other variations and modifications may be made without departing from the spirit of the invention.

It is claimed and desired to secure by Letters Patent:

1. Orthodontic apparatus comprising
a carrier portion including an annular ring fittable on a person's finger unitarily joined with an elongated prong which projects outwardly from a side of the ring, and
a plurality of intraoral orthodontic devices severably joined to and integral with said prong in said carrier portion,
said carrier portion and said devices being formed of an elastomeric material, and said carrier portion being configured to facilitate digital maneuvering of said apparatus to position a device joined to said prong adjacent an orthodontic appliance contained within a person's mouth.

2. The apparatus of claim 1, wherein said devices are joined to said finger through break-away joining structure designed, with snap-action pulling between the finger and a device, to break at a location diposed toward said finger from said device.

3. The apparatus of claim 2, wherein the joining structure for a device comprises an elongated isthmus extending between the device and said finger.

4. The apparatus of claim 3, wherein each isthmus has a rectangular cross section as viewed along a section thereof normal to its longitudinal axis.

5. The apparatus of claim 4, wherein said rectangular cross section is nonsquare.

6. The apparatus of claim 3, wherein each isthmus, as viewed from a side thereof, has a pyramidal configuration including sides which converge progressing along the isthmus from said finger toward the device associated with the isthmus.

7. The apparatus of claim 2, wherein the joining structure for a device comprises means joining the device tangentially with said finger.

8. Molded, unitary, elastomeric orthodontic apparatus comprising
a digitally manipulatable tool portion constructed for placement adjacent and within a person's mouth, and
a plurality of intraoral tension-applying devices severably joined to said tool portion and configured for hooking onto an orthodontic appliance within a person's mouth during placement of a device through manipulation of said tool portion,
severing of a device from said tool portion during placement of a device within a mouth occurring without destruction of the integrity of the tool portion.

9. Molded, unitary, elastomeric orthodontic apparatus comprising
a dispenser portion shaped and constructed for facilitating digital manipulation of the apparatus adjacent the teeth in a person's mouth, and
severably united with and distributed on said dispenser portion a plurality of intraoral tension-applying devices each being configured for hooking onto an orthodontic appliance within a person's mouth through manipulation of said dispenser portion.

10. Orthodontic apparatus comprising
a carrier portion including an endless band fittable on, and manipulatable by, at least a portion of a person's hand for use as a dispensing and placement tool for intraoral orthodontic tension-applying devices,
a plurality of intraoral orthodontic tension-applying devices, each configured for hooking onto an orthodontic appliance within a person's mouth, and
means severably and integrally joining said devices and said carrier portion,
said carrier portion, devices and joining means being formed of a pliable elastomeric material, and
said carrier portion, devices and joining means being so constructed that severing of a device, during use of the apparatus, occurs without affecting the integrity of said carrier portion.

11. A molded, unitary elastomeric construction including combined orthodontic tension-applying devices and an applying tool therefor, said construction comprising
a digitally manipulatable tool portion constructed for placement adjacent and within a person's mouth, and
a plurality of intraoral tension-applying devices severably joined to said tool portion and configured for hooking onto an orthodontic appliance within a person's mouth during placement of a device through manipulation of said tool portion.

* * * * *